United States Patent [19]

Harris

[11] Patent Number: 4,467,817
[45] Date of Patent: Aug. 28, 1984

[54] SMALL DIAMETER LEAD WITH INTRODUCING ASSEMBLY

[75] Inventor: Donald L. Harris, Miami Beach, Fla.

[73] Assignee: Cordis Corporation, Miami, Fla.

[21] Appl. No.: 495,451

[22] Filed: May 18, 1983

Related U.S. Application Data

[63] Continuation of Ser. No. 255,703, Apr. 20, 1981, abandoned.

[51] Int. Cl.³ .............................................. A61N 1/04
[52] U.S. Cl. .................................... 128/786; 128/785; 128/419 P
[58] Field of Search .............................. 128/784–786, 128/419 P, 642; 604/280, 164

[56] References Cited

U.S. PATENT DOCUMENTS

| | | | |
|---|---|---|---|
| 3,087,486 | 4/1963 | Kilpatrick | 128/642 |
| 3,570,485 | 3/1971 | Reilly | 128/214.4 |
| 3,729,008 | 4/1973 | Berkovits | 128/785 |
| 3,827,428 | 8/1974 | Hon et al. | 128/642 |
| 3,844,292 | 10/1974 | Bolduc | 128/418 |
| 3,902,501 | 9/1975 | Citron et al. | 128/418 |
| 3,939,843 | 2/1976 | Smyth | 128/404 |
| 3,976,082 | 8/1976 | Schmitt | 128/418 |
| 4,033,357 | 7/1977 | Helland et al. | 128/418 |
| 4,083,370 | 4/1978 | Taylor | 128/347 |
| 4,142,530 | 3/1979 | Wittkampf | 128/418 |
| 4,144,890 | 3/1979 | Hess | 128/418 |
| 4,146,037 | 3/1979 | Flynn et al. | 128/419 P |
| 4,147,164 | 4/1979 | Behney | 128/76 R |
| 4,154,247 | 5/1979 | O'Neill | 128/419 P |
| 4,166,469 | 9/1979 | Littleford | 128/784 |
| 4,169,479 | 10/1979 | Muto | 128/419 P |
| 4,248,237 | 2/1981 | Kenny | 128/419 P |
| 4,301,815 | 11/1981 | Doring | 128/785 |
| 4,306,562 | 12/1981 | Osborne | 128/214.4 X |
| 4,327,747 | 5/1982 | Gold | 128/784 |

Primary Examiner—Lee S. Cohen
Attorney, Agent, or Firm—Kenway & Jenney

[57] ABSTRACT

A lead for connecting a source of electrical signals to an internal organ of the body. The lead includes a small diameter lead body of carbon filaments surrounded by a stiffening sheath. The stiffening sheath allows the lead with an attached electrode to be guided to the desired internal organ through the vascular system. After the electrode is properly positioned, the sheath is peeled away from the carbon filament lead means of longitudinal grooves extending the length of the lead. The external stiffening sheath eliminates the need for the carbon lead to have a hollow interior for accepting a stylet. The disclosed lead is of small diameter which is particularly advantageous for multiple lead systems.

5 Claims, 5 Drawing Figures

SMALL DIAMETER LEAD WITH INTRODUCING ASSEMBLY

This application is a continuation of application Ser. No. 255,703, filed Apr. 20, 1981, now abandoned.

BACKGROUND OF THE INVENTION

This invention relates to electrical leads, and more particularly to a lead which connects a source of electrical signals to an organ of the body such as the heart.

It is known to stimulate internal body organs such as the heart with electrical signals generated by an electronic device such as a pacemaker. These signals compensate for various cardiac dysfunctions such as rhythm disorders. Generally, the pacing device itself is located some distance away from the organ needing stimulation and is connected to the organ by an electrical lead.

One way of establishing electrode contact with heart muscle is to feed the electrode and its lead through the venous system into the heart. It is necessary in this case that the lead have sufficient stiffness and maneuverability to negotiate the various turns encountered in the journey through the venous system to the heart. It is also desirable that a stimulating lead have small diameter for ease of introduction into the vascular system and also for the ready accommodation of multiple lead systems. In the prior art, it is known to employ a lead with a central hole or lumen. A relatively stiff stylet is inserted into the lumen as an aid for feeding the lead through the venous system. That such prior art leads had a central lumen created by spirally winding the lead conductor around a mandrel which in turn caused the overall lead diameter to be larger than would have been the case without the stylet-receiving lumen. It is known also in the prior art to surround a lead with a stiffening external sheath so as to eliminate a diameter-increasing lumen. These known attempts using an external sheath, however, have not been acceptable because they also required a relatively large diameter. In addition, appropriate stiffness was difficult to achieve and the sheath often kinked because of the sharp bending required to reach a desired location within the heart.

The electrodes on the distal ends of prior art stimulating leads often comprise a cylindrical body having protruding fins for attachment to the organ needing stimulation. These prior art electrodes were of relatively large diameter requiring a large inside diameter introducer for entry into the vascular system.

It is, therefore, an object of the present invention to provide a stimulating lead which has a small diameter resulting from the elimination of the central stylet-receiving lumen.

It is a further object of the present invention to provide a lead having a distal tip of small diameter.

It is yet another object of this invention to provide a lead which is not only very small in diameter but also is extremely rugged and capable of long operating life.

SUMMARY OF THE INVENTION

The lead according to the present invention for connecting a source of electrical signals to an internal organ of the body comprises a plurality of conductive carbon filaments within an insulating cover assembled to form a lead body. An electrode secured to the distal end of the lead is adapted for connection to the organ and a connector disposed at the proximal end of the lead is adapted for connection to the signal source. A stiffening sheath for guiding the lead through the venous system to the organ surrounds the lead body. This sheath is adapted for peeling away from the lead after connection of the electrode to the organ.

In a preferred embodiment, the sheath has a pair of longitudinally extending separating grooves so as to allow the sheath to be peeled from the lead. In this embodiment, the electrode tip includes a body portion and a plurality of hooking fins extending radially from the body portion for attachment of the electrode to the organ. These fins are adapted for folding around the body portion without overlap for introduction into the vascular system so as to minimize the diameter of the tip. After introduction, the fins extend due to their intrinsic resilience. In these embodiments it is preferred that the stiffening sheath be made of a polyethylene material.

BRIEF DESCRIPTION OF THE DRAWING

The invention disclosed herein may be better understood with reference to the following drawing of which.

DESCRIPTION OF THE PREFERRED EMBODIMENT

Figure 1:
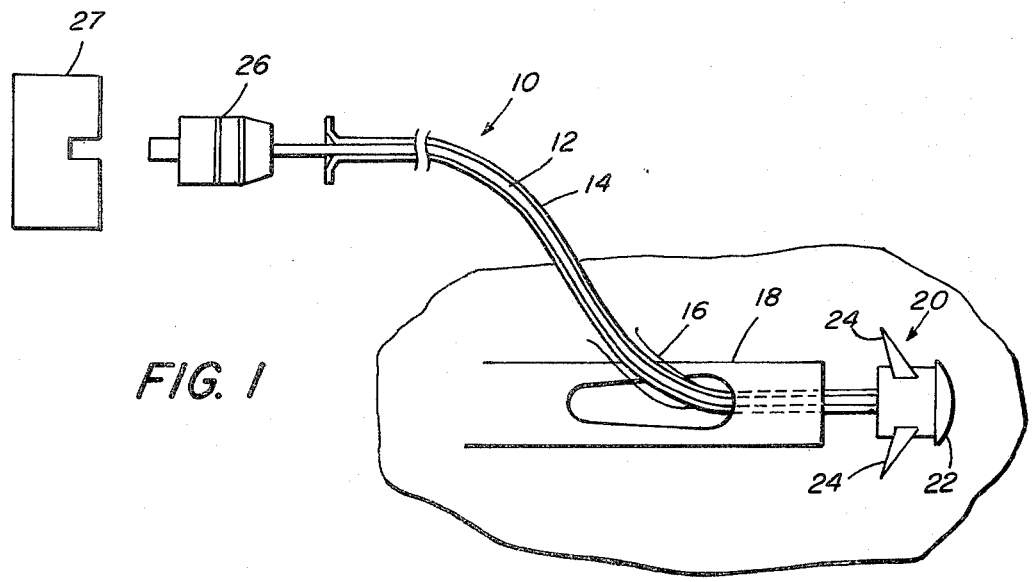
FIG. 1 is a diagrammatic representation, to enlarged scale, of the lead assembly disclosed herein being introduced into the vascular system.

With reference first to FIG. 1, the small diameter carbon lead with introducing assembly is designated generally at 10. The lead assembly 10 includes a multifilament, small diameter carbon lead body 12 surrounded by a stiffening sheath 14. As illustrated, the lead assembly 10 has been inserted through an introducing assembly 16 into a vessel 18 of the vascular system. The distal end of the lead assembly 10 terminates with an electrode assembly 20 which includes a body portion electrode 22 and hooking fins 24 for attaching the electrode tip assembly 20 to an organ of the body such as to the trabeculae of the heart. The proximal end of the lead assembly 10 terminates in a connector 26 which is adapted for attachment to a source of electrical signals such as a conventionally known cardiac pacing apparatus 27.

Figure 2:
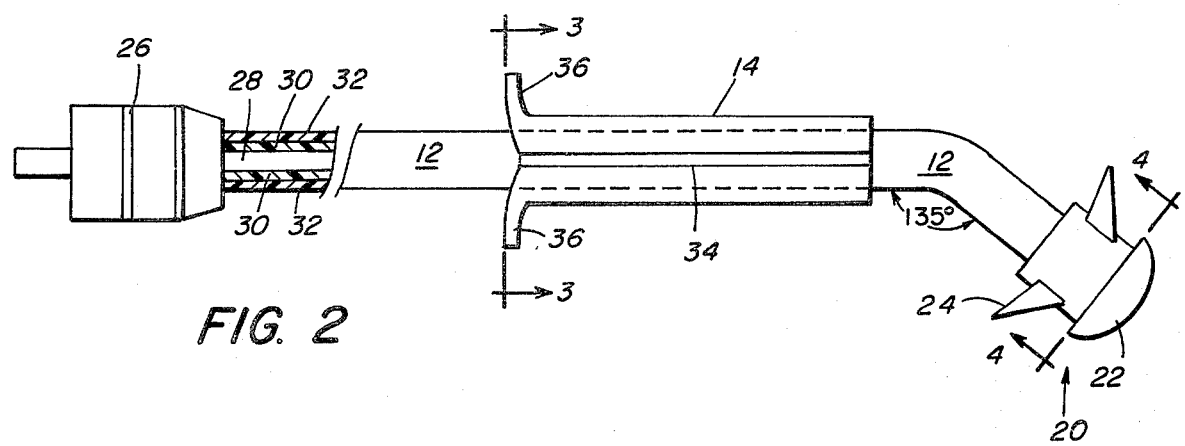
FIG. 2 is a diagrammatic representation, to even larger scale, of the present lead.

The lead disclosed herein is shown in more detail in FIG. 2. The multifilament carbon lead body 12 of the lead and introducer assembly 10 has a small diameter of approximately 0.053 inches which corresponds to a French 4 diameter. The lead body 12 is composed of a core 28 comprising approximately 3,000 carbon fibers in a high modulus graphite filament form. Suitable fiber material is available from the Union Carbide Corporation under the trademark "Thornel" and is designated as 300 WYP 30 1/0 with a special resin matrix added. Under this designation, the fibers have been embedded in a resin matrix composed of tetrafluoroethylene mixed with a small proportion of urethane as described in U.S. Pat. No. 4,198,991, entitled "Cardiac Pacer Lead", the teachings of which are incorporated herein by reference. The core 28 is then pulled into a thin-walled tube 30 of polytetrafluoroethylene manufactured by Dupont and designated 6C having good lubricity and long flex life both to contain the fibers and to act as an electrical insulator. The combination of the tubing and resin matrix prevents the fibers from breaking or otherwise destroying one another as the thread 12 flexes both during introduction into the vascular system and thereafter during its intended operation. The core 28 and tube 30 assembly is next pulled into a body compatible polyurethane tube 32. A suitable tube 32 material is available from Mobay Chemical Corporation of Pittsburgh, Pa. under the designation Texin 85-A. The polyurethane tube 32 is first allowed to expand in chlorothene for fifteen to thirty minutes before being pulled over the core 28-tube 30 assembly. The polyurethane tube 32 is then allowed to shrink by exposure to air. The lead body 12 is thus of solid construction since a hollow interior is not needed as in the prior art systems which use an introducing stylet to guide the lead to the organ for stimulation.

The multifilament carbon thread 12 is closely surrounded by a sheath 14 which is adapted to stiffen the thread 12 for introduction into and guidance through the vascular system. The sheath 14 is a substantially cylindrical jacket preferably made of a high density polyethylene such as Marlex HHM 4903 available from Phillips Petroleum, and compounded with approximately 10% barium sulphate and 1% titanium dioxide to make the sheath radiopaque and white. The sheath 14 slides over the thread 12 at the time that the lead assembly 10 is assembled. The sheath 14 has a wall thickness of approximately 0.0065 inch, so that the combined thread 12 and sheath 14 diameter is approximately 0.066 inches corresponding to a French 5 diameter. The sheath 14 provides the necessary stiffness so that the lead assembly 10 may be guided through the vascular system to the heart, for example. That is, because the inside diameter of the sheath 14 is smaller than the electrode assembly 20 diameter (approximately 0.079 inch), the sheath 14 acts as a pusher for guiding the assembly 20 to the target organ. After the sheath 14 is assembled onto the thread 12, the electrode assembly 20 and connector 26 are affixed to the distal and proximal ends of the thread 12 respectively in an electrically conducting relation in the manner described in the above-mentioned U.S. Pat. No. 4,198,991.

Figure 3:
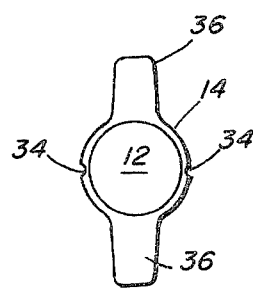
FIG. 3 is a cross-sectional view along section lines 3—3 of FIG. 2.

The sheath 14 serves merely as an aid in guiding the lead assembly 10 through the vascular system to the target organ; it must be removed once the electrode assembly 20 is properly positioned. It cannot be removed by sliding it off because its diameter is much smaller than that of the connector 26 over which it would have to be removed. (It could be removed by sliding it from the thread 12 if the connector 26 were not attached to the thread 12 until the lead assembly 10 had been positioned within the body. However, the connector 26 then would have to be attached to the thread 12 in the midst of a sterile procedure, a practical impossibility.) According to the present invention, the sheath 14 is rendered readily removable by providing it with longitudinally extending separating grooves 34, FIGS. 2 and 3, which allow the sheath 14 to be peeled apart by grasping the handles 36 and pulling gently. The handles 36 are molded onto the sheath 14. The grooves 34 are approximately 0.004 inch deep so that the sheath 14 will separate readily.

The electrode tip assembly 20 plays an important role in keeping the overall diameter of the lead assembly disclosed herein relatively small. Although the diameter of the electrode assembly 20 is larger than the diameter of the lead body 12, its length is very short in comparison with the lead assembly 10 so that maintaining the lead body 12 diameter small is particularly advantageous in multiple lead systems. The electrode tip assembly 20 comprises the electrode body 22 which is adapted for engaging the organ to be stimulated in an electrically conducting relationship. The electrode body 22 is of conventional design with a diameter of approximately 0.079 inch and may be porous or nonporous. A suitable material is elgiloy or platinum, or even an extension of the carbon fibers themselves. The electrode tip assembly 20 is attached to the organ, for example the heart, by means of the hooking style fins 24 which grab onto the heart trabeculae thereby immobilizing the tip assembly 20 with respect to the heart muscle. The tip assembly 20 can be seen more clearly with reference to FIG. 4. The three hooking fins 24 are made of a thin, flexible material such as silastic or polyurethane and are of a length of approximately 0.08 inch so that they can be wrapped around the electrode tip body 22 without overlap for introduction into the venous system through a small diameter introducing assembly 16 as shown in FIG. 1. Because the fins wrap around the electrode without overlap, the diameter is small enough so that it may be inserted through an introducing assembly used for a French 7 diameter lead. Once the electrode tip assembly 20 has passed through the introducing assembly, the resilient fins 24 return to their extended state.

Figure 4:
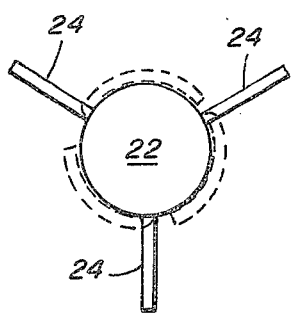
FIG. 4 is a cross-sectional view along section lines 4—4 of FIG. 2.
Figure 5:
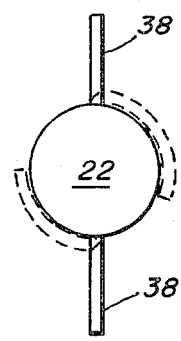
FIG. 5 is an alternate embodiment of the electrode tip disclosed herein.

FIG. 5 illustrates another embodiment of the electrode assembly 20 including two hooking fins 38 instead of three as shown in FIG. 4. The hooking fins 38 of FIG. 5 have a length of approximately 0.125 inch so that they do not overlap when they are wrapped around the electrode assembly body 22.

In operation, the small diameter lead assembly 10 along with the electrode tip assembly 20 is introduced through an introducing assembly 16 into a vessel such as shown at 18 in FIG. 1. The lead assembly 10 with the attached electrode tip assembly 20 is then fed through the vascular system and guided toward the desired organ by means of the stiffening sheath 14. When the heart is the target organ, the lead assembly 10 is advanced to the vicinity of the tricuspid valve. Because of the location of the tricuspid valve, it is necessary that the lead assembly 10 have a bend in it so that it can be located and pass through. In prior art devices the stylet which rested within an internal lumen of a carbon lead was itself bent to enable passage through the tricuspid valve.

In the present embodiment, however, since there is no introducing stylet, a portion of the carbon thread 12 itself about 5 cm. from its distal end will have a preformed curve as can be seen in FIG. 2. This pre-formed curve is created by heating the lead assembly 10 in a form so that the tubing over the fibers will take a set upon cooling. While the stiffening sheath 14 covers this pre-formed portion, however, the lead 10 is straightened. In the vicinity of the tricuspid valve, the stiffening sheath 14 is retracted somewhat away from the electrode assembly 22 by means of the handles 36 so that the carbon thread 12 assumes the proper curved shape to locate the passage through the tricuspid valve. Once the lead assembly 10 has been advanced through this valve, the sheath 14 is advanced to cover the lead body 12 again to straighten it for its final positioning within the heart. At the desired location, the hooking fins 24 engage the trabeculae of the heart and are held firmly in place as fibrosis occurs. After the electrode assembly is securely in place, the stiffening sheath, having performed its function of guiding the lead assembly 10 to the target organ, is peeled apart as it is withdrawn from the vessel 18 (FIG. 1). The carbon lead body 12 and the electrode tip assembly 20 remain in the body. If it is desired to remove the lead assembly 10 at some later time, the lead may be twisted, thereby wrapping the fins around the electrode so that it can be repositioned or withdrawn.

It is thus seen that the objects of this invention have been achieved in that there has been described a small diameter carbon lead with an external stiffening sheath to aid in its journey through the venous system to a target organ. The use of the external stiffening sheath eliminates the need for the carbon lead itself to have a hollow interior to accommodate a stylet as known in prior art systems thereby resulting in a lead with a smaller overall diameter.

Although this invention has been described with reference to specific embodiments, it is understood that modifications and variations will occur to those skilled in the art. It is intended that all such modifications and variations be included within the scope of the appended claims.

What is claimed is:

1. A pervenous lead system for establishing electrical contact between an electrical stimulation generator and an internal organ, comprising
   an implantable lead with proximal and distal ends having a flexible insulated hollow lead body carrying at least one electrical conductor substantially occupying the lumen of said body, said lead having a portion of enlarged diameter toward the distal end and an organ-contacting electrode electrically connected to said conductor,
   removable flexible sleeve means slidably mounted on said lead body for applying axial force directly to the enlarged distal portion of said lead while traveling through a blood vessel, and
   means at the proximal end for connecting said conductor to the generator,
   whereby the lead can be urged flexibly through a blood vessel with stylet-like action by externally manipulating said sleeve means.

2. The lead system of claim 1, wherein said sleeve means includes a flexible guide sleeve disposed coaxially and slidably over substantially the entire length of said lead body with a uniform inner diameter between those of said lead body and the enlarged distal portion of said lead such that said sleeve is slidable into abutment with the enlarged distal portion of said lead so as to drive it forward when the sleeve is advanced from the proximal end.

3. The lead system of claim 2, wherein said connecting means includes a connector assembly electrically connected to said conductor adapted to be received by said generator, said sleeve having means defining at least one weakening line extending longitudinally from the proximal to the distal end of said sleeve such that the sleeve can be split open and peeled off of said lead body without interfering with the connector assembly as the sleeve is withdrawn.

4. The lead system of claim 3, wherein said sleeve includes at its proximal end integral handle means for manipulating said sleeve and aiding in its ultimate removal.

5. The lead system of claim 1, wherein a portion of the distal end of said lead is resiliently pre-bent in an obtuse angle, the relative flexibility of said lead and said sleeve means being such that the pre-bent portion is substantially straightened when the sleeve means is advanced over the pre-bent portion of the lead toward the enlarged distal portion thereof,
   whereby, in order to navigate complex passages of the vascular system, the pre-bent portion of the lead can be deployed temporarily by retracting the sleeve means.

* * * * *